US009149669B2

(12) United States Patent
Cowell et al.

(10) Patent No.: US 9,149,669 B2
(45) Date of Patent: Oct. 6, 2015

(54) RESPIRATORY PROTECTION DEVICE HARNESS ASSEMBLY

(71) Applicant: 3M INNOVATIVE PROPERTIES COMPANY, St. Paul, MN (US)

(72) Inventors: Michael J. Cowell, Woodbury, MN (US); William A. Mittelstadt, Woodbury, MN (US); Carl W. Raines, III, Woodbury, MN (US); Thomas G. Skulley, St. Paul, MN (US); Nathan A. Abel, Minneapolis, MN (US); Fredrik Ericsson, Nacka (SE); Ayden Mert, Stockholm (SE); August Michael, Enskede (SE); Oskar Juhlin, Gustavsberg (SE)

(73) Assignee: 3M Innovative Properties Company, St. Paul, MN (US)

( * ) Notice: Subject to any disclaimer, the term of this patent is extended or adjusted under 35 U.S.C. 154(b) by 349 days.

(21) Appl. No.: 13/757,337

(22) Filed: Feb. 1, 2013

(65) Prior Publication Data

US 2014/0216463 A1    Aug. 7, 2014

(51) Int. Cl.
*A62B 18/08* (2006.01)
*A41D 13/11* (2006.01)
*A61M 16/06* (2006.01)

(52) U.S. Cl.
CPC ........... *A62B 18/084* (2013.01); *A41D 13/1161* (2013.01); *A61M 16/0683* (2013.01)

(58) Field of Classification Search
CPC .... A44B 11/25; A44B 11/2592; A41D 13/11; A41D 13/05; A41D 13/1146; A62B 18/08; A62B 18/00; A62B 18/084; A62B 18/025; A61M 11/00; A61M 16/06; A61M 16/0683

USPC ................. 128/863, 206.27, 206.28, 207.11, 128/205.25, 201.25, 206.17, 201.19; 24/625
See application file for complete search history.

(56) References Cited

U.S. PATENT DOCUMENTS 3,605,204 A    3/1970  Amundsen
3,594,816 A *  7/1971  Webb et al. ........................ 2/10
(Continued)

FOREIGN PATENT DOCUMENTS

CA    2 402 743    10/2001
CN    2800855    6/2005
(Continued)

OTHER PUBLICATIONS

International Application PCT/US2014/012500 Search Report dated Nov. 17, 2014.

*Primary Examiner* — Annette Dixon
(74) *Attorney, Agent, or Firm* — Peter L. Olson

(57) ABSTRACT

A harness assembly for a respiratory protection device is provided. In an exemplary embodiment, the harness assembly includes a strap support having an attachment point, a first strap having a first strap attachment element, and a second strap having a second strap attachment element, wherein the first strap attachment element is attachable to the second strap attachment element and attachable to the attachment point of the strap support, and the first and second straps are positionable between the first configuration in which the first strap attachment element is attached only to the second attachment element and a second configuration in which the first attachment element is attached to the second attachment element and the attachment point of the strap support.

24 Claims, 8 Drawing Sheets

(56) References Cited

U.S. PATENT DOCUMENTS

| | | | | |
|---|---|---|---|---|
| 3,786,519 | A | * | 1/1974 | Aileo ................................. 2/6.2 |
| 3,789,427 | A | * | 2/1974 | Aileo ................................. 2/423 |
| 3,852,821 | A | * | 12/1974 | Mickel ............................... 2/415 |
| 3,906,547 | A | * | 9/1975 | Aileo ................................. 2/422 |
| 4,023,209 | A | * | 5/1977 | Frieder et al. ...................... 2/6.6 |
| 4,727,629 | A | * | 3/1988 | Hoen et al. ........................ 24/458 |
| 4,777,704 | A | * | 10/1988 | Acker .............................. 24/106 |
| 4,843,688 | A | | 7/1989 | Ikeda |
| H0001039 | H | * | 4/1992 | Tripp et al. .............. 128/206.28 |
| 5,566,427 | A | | 10/1996 | Lathrop |
| 5,727,259 | A | | 3/1998 | Kawamata |
| 6,062,221 | A | | 5/2000 | Brostrom |
| 6,457,473 | B1 | | 10/2002 | Brostrom |
| 6,691,377 | B2 | | 2/2004 | Pan |
| 6,691,378 | B1 | | 2/2004 | Chou |
| 6,694,532 | B2 | | 2/2004 | Chen |
| 6,732,733 | B1 | | 5/2004 | Brostrom |
| 7,296,305 | B2 | | 11/2007 | Ketterer |
| 7,340,804 | B2 | | 3/2008 | Saderholm |
| 8,132,603 | B2 | | 3/2012 | Hogan |
| 8,505,536 | B2 | | 8/2013 | Kielow |
| 2004/0016057 | A1 | * | 1/2004 | Traut et al. ........................ 5/628 |
| 2011/0220115 | A1 | | 9/2011 | Castiglione |
| 2012/0222202 | A1 | | 9/2012 | Chang |
| 2012/0266418 | A1 | | 10/2012 | Chou |

FOREIGN PATENT DOCUMENTS

| | | |
|---|---|---|
| DE | 642 683 | 2/1937 |
| DE | 9300181 | 1/1993 |
| DE | 9419623 | 3/1995 |
| DE | 29517776 | 3/1996 |
| EP | 1 001 830 | 3/2004 |
| GB | 523822 | 1/1939 |
| GB | 2042054 | 1/1980 |
| GB | 2202130 | 9/1988 |
| GB | 2 338 787 | 4/2003 |
| GB | 2 454 451 | 10/2010 |
| GB | 2 477 738 | 8/2012 |
| GB | 2 489 045 | 3/2013 |
| WO | WO 99/06116 | 2/1999 |
| WO | WO 2012/100116 | 7/2012 |

* cited by examiner

RESPIRATORY PROTECTION DEVICE HARNESS ASSEMBLY

TECHNICAL FIELD

This disclosure relates to a harness assembly, in particular a harness assembly for a respiratory protection device including a first strap attachment element attachable to a second strap attachment element and an attachment point of a strap support.

BACKGROUND

Respiratory protection devices that cover a user's nose and mouth, for example, and provide filtered air to a wearer are well known. Air is drawn through a breathable air source by a negative pressure generated by a wearer or forced into a breathing zone by a fan or blower, for example, where it may be inhaled by the wearer.

Various strap configurations and harness assemblies have been provided for positioning and maintaining a respiratory protection device over the nose and mouth of a wearer. For example, some harness assemblies may include one or more tensioned straps that pass behind a wearer's neck such that the respiratory protection device is drawn over the wearer's nose and mouth. Other harness assemblies may include a support member that may rest on a wearer's head and that one or more straps may be attached to in order to maintain the respiratory protection device in a desired position.

SUMMARY

The present disclosure provides a harness assembly for a respiratory protection device including a strap support having an attachment point, a first strap having a first strap attachment element, and a second strap having a second strap attachment element. The first strap attachment element is attachable to the second strap attachment element and attachable to the attachment point of the strap support, and the first and second straps are positionable between a first configuration in which the first strap attachment element is attached only to the second attachment element and a second configuration in which the first attachment element is attached to the second attachment element and the attachment point of the strap support. In an exemplary embodiment, the first attachment element is rotatable relative to the second attachment element when the first and second attachment elements are attached.

The present disclosure further provides a harness assembly for a respirator including a strap support positionable about a crown of a wearer's head and having first and second upper attachment points and a central lower attachment point, first and second upper straps attachable to the first and second upper attachment points, a first lower strap having a first strap attachment element, and a second lower strap having a second strap attachment element. The first strap attachment element is attachable to the second attachment element and attachable to the lower attachment point of the strap support, and the first and second lower straps are positionable between a first configuration in which the first strap attachment element is attached only to the second attachment element and a second configuration in which the first attachment element is attached to the second attachment element and the lower attachment point.

The present disclosure further provides a harness assembly for a respirator including a first lower strap having a first strap attachment element having a first ring defining a first central opening and a second lower strap having a second strap attachment element having a second ring defining a second central opening. The first strap attachment element is attachable to the second attachment element such that the first strap attachment element may rotate relative to the second strap attachment element when the first and second attachment elements are attached, and the first and second central openings are substantially aligned when the first and second strap attachment elements are attached.

The above summary is not intended to describe each disclosed embodiment or every implementation. The Figures and the Detailed Description, which follow, more particularly exemplify illustrative embodiments.

BRIEF DESCRIPTION OF DRAWINGS

The disclosure may be further explained with reference to the appended Figures, wherein like structure is referred to by like numerals throughout the several views, and wherein.

While the above-identified figures set forth various embodiments of the disclosed subject matter, other embodiments are also contemplated. In all cases, this disclosure presents the disclosed subject matter by way of representation and not limitation. It should be understood that numerous other modifications and embodiments can be devised by those skilled in the art which fall within the scope and spirit of the principles of this disclosure.

DETAILED DESCRIPTION

The present disclosure provides a respiratory protection device harness assembly. The harness assembly comprises a strap support having an attachment point, a first strap having a first strap attachment element and a second strap having a second strap attachment element. The first strap attachment element is attachable to the second attachment element and attachable to the attachment point of the strap support. First and second straps are positionable between a first configuration in which the first strap attachment element is attached only to the second strap attachment element and a second configuration in which first strap attachment element is attached to the second strap attachment element and the attachment point of the strap support. An exemplary harness assembly according the present disclosure thus allows a wearer to choose between a first configuration in which the first and second straps pass behind the wearer's neck when the first and second attachment elements are attached to one another, or a second configuration in which the first and second straps and strap attachment elements are raised above the wearer's neck and attached to an attachment point of the strap support. Both the first and second configurations of the harness assembly allow a respiratory protection device to be appropriately positioned over the nose and mouth of a wearer to deliver breathable air to the wearer.

Figure 1:
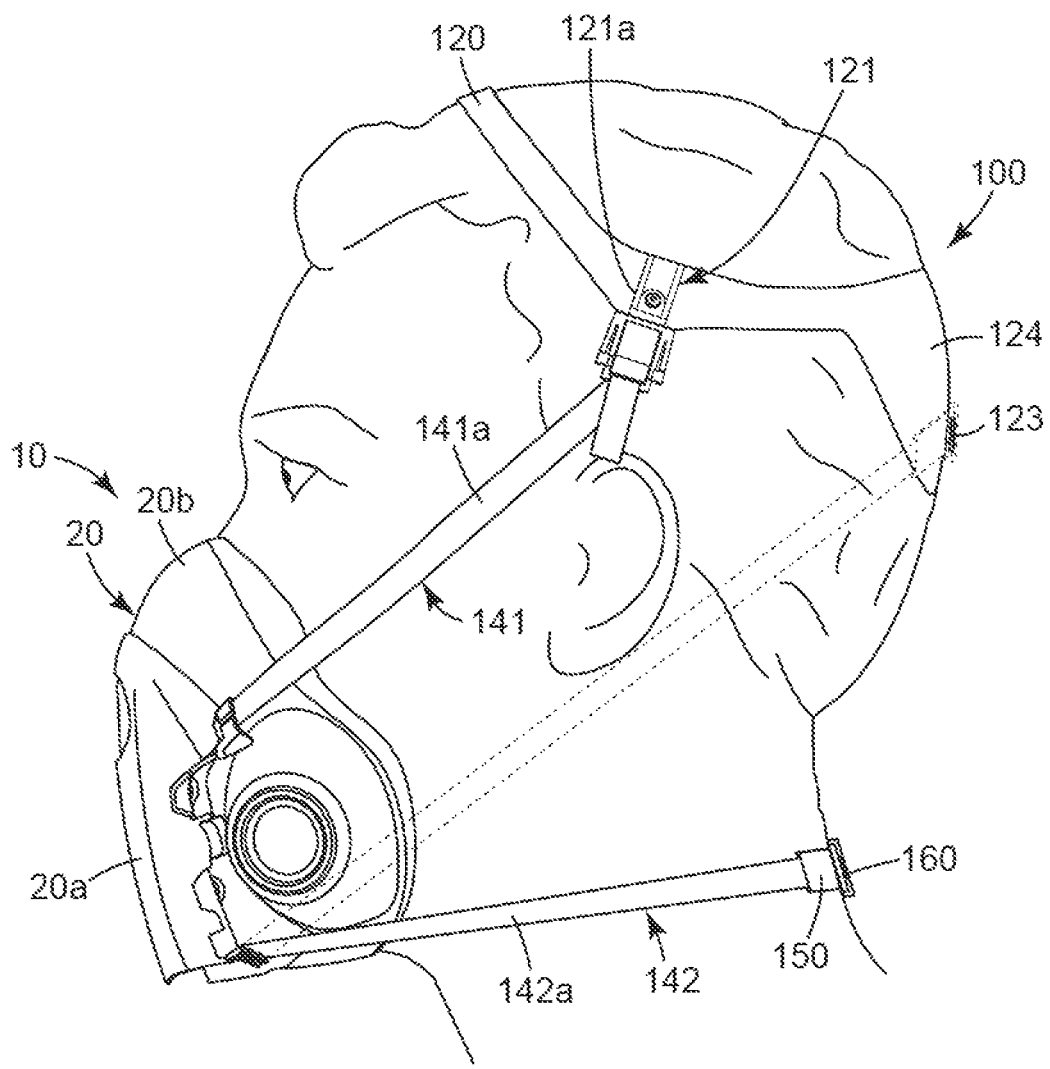
FIG. 1 shows a side view of an exemplary personal protective device including a harness assembly according to the present disclosure.

FIG. 1 shows an exemplary respiratory protection device 10 including an exemplary harness assembly 100 according to the present disclosure. Respiratory protection device 10 includes a mask body 20. Mask body 20 may include a rigid or semi-rigid portion 20a and a face contacting portion 20b. Face contacting portion 20b may be formed of a soft or compliant material that provides a comfortable fit and is able to seal against the face of a wearer to prevent ingress of external air. Harness assembly 100 may include one or more straps, such as upper straps 141 and lower straps 142, to secure respiratory protection device 10 in a position of use over the nose and mouth of the wearer. Upper straps 141 and lower straps 142 may be portions of a single continuous integral strap that passes through a loop or attachment element of mask body 20, for example, or may be discrete individual straps that are each attached to mask body 20. In an exemplary embodiment, harness assembly 100 includes a strap support 120 configured to fit generally about the crown of a wearer's head. Upper and lower straps 141, 142 may be appropriately tensioned such that face contacting portion 20b of mask body 20 is adequately positioned and/or sealed against a wearer's face.

Strap support 120 may exhibit any desired shape that may be positioned about the crown or top portion of a wearer's head and that one or more straps may be attached to. In some embodiments, strap support 120 includes one or more of a plastic, foam, elastomeric polymer, leather, fabric, mesh, or other suitable materials. Strap support may also provide a support for a head covering, such as a hard hat, respirator hood, or other head covering. In other exemplary embodiments, strap support 120 is a head covering such as a cap, hard hat, hood, beanie, netting or other suitable head covering that may be positioned about the crown or top portion of a wearer's head and that may allow attachment of one or more straps.

In an exemplary embodiment, strap support 120 includes one or more upper attachment points 121. One or more upper straps 141 may be attached to the one or more upper attachment points 121. In an exemplary embodiment, harness assembly 100 includes a first upper strap 141 a extending from mask body 20 in front of and/or over a wearer's ear and attached to a first upper attachment point 121a of strap support 120, and a second upper strap (not shown) extending from mask body 20 in front of and/or over a wearer's opposite ear and attached to a second upper attachment point (not shown) of strap support 120. Harness assembly 100 further includes a first lower strap 142a having a first strap attachment element 150 and a second lower strap (not shown) having a second strap attachment element 160. Strap support 120 further includes a lower attachment point 123. In an exemplary embodiment, attachment point 123 is centrally located on a downwardly extending lower portion 124 of strap support 120. First and second strap attachment elements 150, 160 securely maintain first and second lower straps at a desired length and may allow adjustment of the lower straps. As will be described in greater detail below, first strap attachment element 150 is attachable to second strap attachment element 160 and attachable to the lower attachment point 123 of strap support 120. First and second lower straps are thus positionable between at least a first configuration (shown in solid) in which first strap attachment element 150 is attached only to the second strap attachment element 160, and a second configuration (shown in phantom) in which first strap attachment element 150 is attached to second strap attachment element 160 and lower attachment point 123 of strap support 120.

Figure 2:
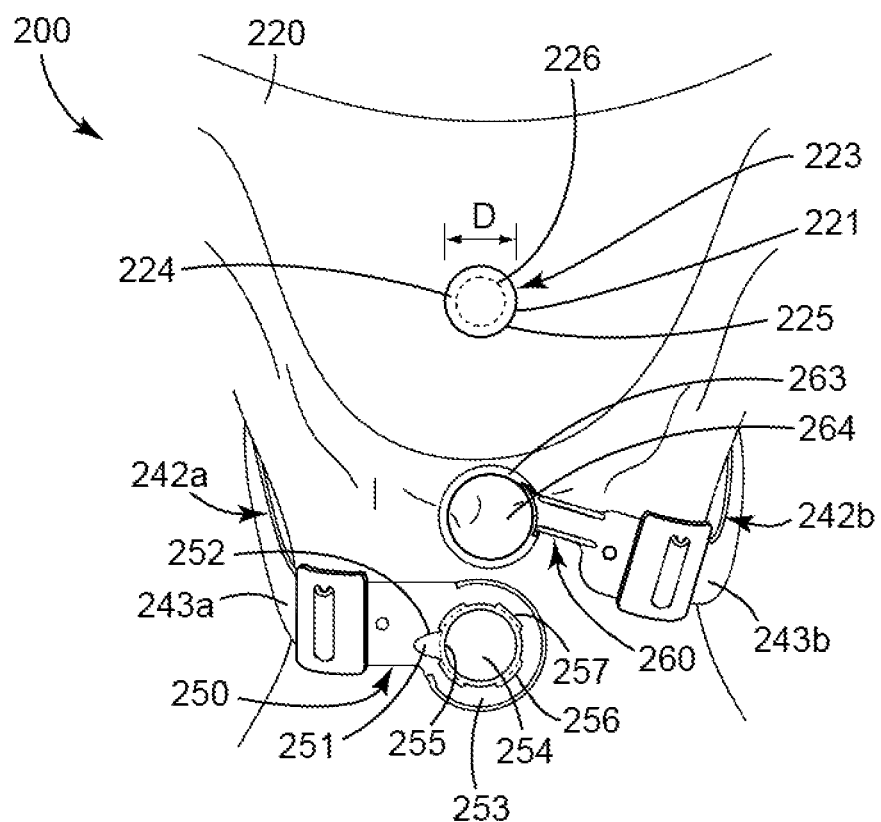
FIG. 2 shows a rear view of an exemplary harness assembly according to the present disclosure having exemplary first and second strap attachment elements in an unattached configuration.
Figure 3:
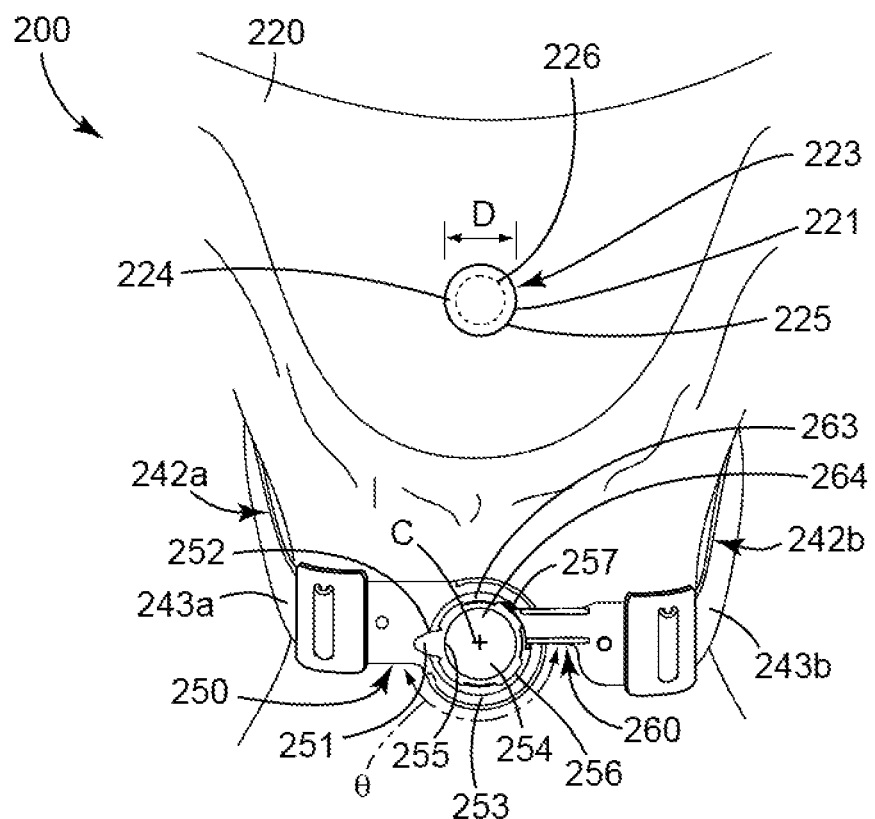
FIG. 3 shows a rear view of an exemplary harness assembly according to the present disclosure having exemplary first and second strap attachment elements in a first configuration in which the first and second strap attachment elements are attached.
Figure 4:
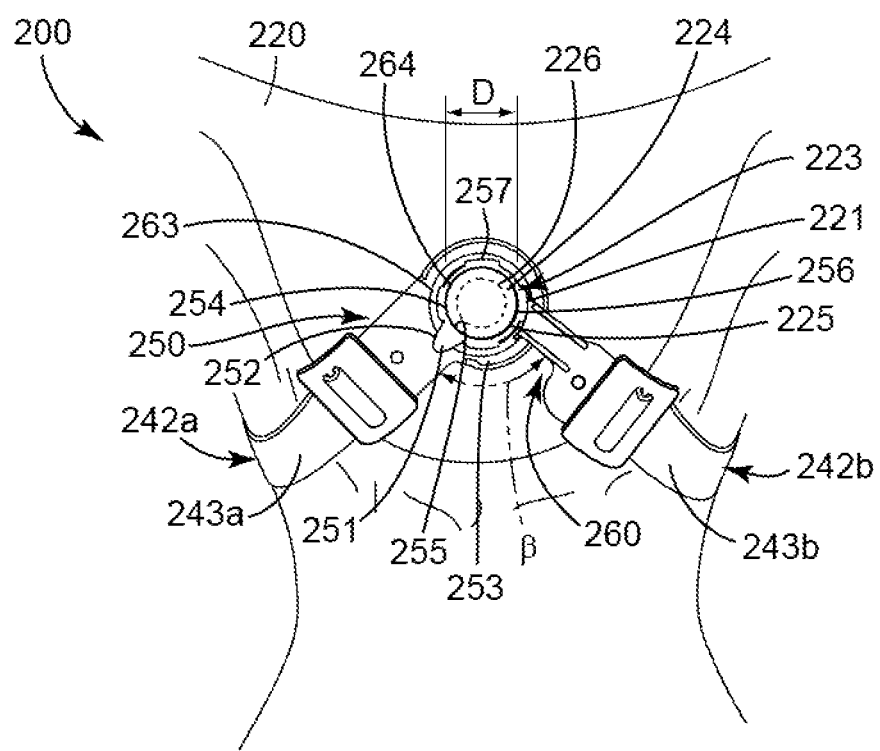
FIG. 4 shows a rear view of an exemplary harness assembly according to the present disclosure having exemplary first and second strap attachment elements in a second configuration in which the first attachment element is attached to the second attachment element and an attachment point of a strap support.

FIGS. 2, 3 and 4 show rear views of an exemplary embodiment of a harness assembly 200 including a strap support 220 having a lower attachment point 223, first lower strap 242a having a first strap attachment element 250, and second lower strap 242b having a second strap attachment element 260. FIG. 2 shows first and second straps 242a, 242b in an unattached configuration, just before being attached when a wearer is donning harness assembly 200 and a respiratory protection device (not shown), for example. FIG. 3 shows first and second straps 242a, 242b in a first configuration in which the first and second strap attachment elements 250, 260 are attached and a respiratory protection device, for example, may be maintained in a position of use over a nose and mouth of a wearer. FIG. 4 shows first and second straps 242a, 242b in a second configuration in which first strap attachment element 250 is attached to second strap attachment element 260 and to attachment point 223 of strap support 220 and a respiratory protection device, for example, may be maintained in a position of use over a nose and mouth of a wearer.

First and second straps 242a, 242b include first and second strap attachment elements 250 and 260 proximate first and second end portions 243a, 243b. Straps 242a, 242b are secured to first and second attachment elements such that a desired length of straps 242a, 242b may be provided. In some exemplary embodiments, the length of straps 242a, 242b may be adjusted such that the length of straps 242a, 242b are increased or decreased, and the straps made looser or tighter, for example, when harness assembly 200 is positioned for use.

First strap attachment element 250 is attachable to second strap attachment element 260 and attachment point 223 of strap support 220. In an exemplary embodiment, first strap attachment element 250 includes first and second attachment features such that the first attachment feature is attachable to a complementary feature of the second strap attachment element and the second attachment feature is attachable to attachment point 223. For example, first strap attachment element 250 may comprise a first attachment feature in the form of hook 251 defining a channel 252. In other exemplary embodiments, first attachment feature may be in the form of a loop, tab, flanged projection, receptacle, or other suitable attachment feature.

In an exemplary embodiment, first strap attachment element 250 includes a first ring 253 defining a first central opening 254. A hook 251 is positioned proximate ring 253 and extends generally upwardly and outwardly from an inner peripheral edge 255 of ring 253. In some embodiments, ring 253 includes a groove or recess 256 sized to receive a portion of second strap attachment element 260, and a flange 257 may extend about at least a portion of groove or recess 256.

Second strap attachment element 260 includes one or more attachment features having a shape complementary to an attachment feature of first strap attachment element 250. In an exemplary embodiment, second strap attachment element 260 includes a second ring 263 defining a second opening 264. A portion of ring 263 is positionable within or about hook 251 and/or channel 252 to attach first strap attachment element 250 and second strap attachment element 260.

In some exemplary embodiments, first and second strap attachment elements 250, 260 may be permanently attached, such that separation may be impossible, or may be possible only by damaging one or both of first and second strap attachment elements 250, 260. Rather than attaching the first and second strap attachment elements 250, 250 each time a wearer dons or doffs the harness assembly, the wearer could place the loop formed by the first and second lower straps 242a, 242b and permanently attached first and second strap attachment elements 250, 260 over the head and around the neck, for example.

Strap support 220 includes a lower attachment point 223 to which a strap attachment element may be attached. Lower attachment point 223 is positioned at a generally central location on strap support 220. For example, lower attachment point may be positioned proximate a sagittal plane (not shown), for example, that divides a wearer's head into imaginary left and right halves. A generally centrally located attachment point 223 allows both of first and second attachment elements to be attached to strap support 220 at a single location while first and second straps exhibit a similar length. In the exemplary embodiment of FIGS. 2 through 4, lower attachment point 223 is a flanged projection extending outwardly from strap support 220. Lower attachment point 223 may have a generally cylindrical shape, for example. In some embodiments, lower attachment point 223 includes a flanged edge 224 such that a diameter D at an outer portion 225 is greater than a diameter at a middle or inner portion 226. An opening or recess of a strap attachment element may be positioned over the flanged projection to attach one or more strap attachment elements to lower attachment point 223, as described in greater detail below. In other exemplary embodiments, a lower attachment point 223 may be provided in the form of a hook, loop, receptacle, shelf, projection, flange or other suitable attachment point such that one or more strap attachment elements may be attached to strap support 220. In some exemplary embodiments, an additional lower attachment point may provided for attaching one or more lower straps and strap attachment elements.

FIG. 3 shows first and second straps 242a, 242b in a first configuration in which the first and second strap attachment elements 250, 260 are attached. First and second straps 242a, 242b are tensioned such that a respiratory protection device (not shown), for example, is maintained in a position of use over a nose and mouth of a wearer. A portion of ring 263 is positioned within channel 252 of hook 251, and ring 263 may further be positioned in groove 256. In an exemplary embodiment, tension of first and second lower straps 242a, 242b provides a force on the portion of ring 263 towards channel 252 and prevents disengagement between first and second strap attachment elements 250, 260. Hook 251, groove 256, and/or other features of first and second attachment elements maintain first and second central openings 254, 264 in substantial alignment. That is, first and second central openings 254, 264 at least partially or at least mostly overlap. In an exemplary embodiment, first and second central openings 254, 264 concentrically overlap, such that first and second central openings share a center C.

First and second strap attachments elements 250, 260 are rotatable when attached. That is, first strap attachment element 250 may rotate relative to second strap attachment element 260 when first and second strap attachment elements 250, 260 are attached. Rotatable first and second strap attachment elements 250, 260 allow first and second straps 242a, 242b to be positioned naturally about the wearer's neck, and to be positionable between multiple configurations. Although straps 242a, 242b are generally made of a flexible, elastic material, the rotatable strap attachment elements prevent straps from bunching and/or creating points of high pressure that could cause first and/or second strap attachment elements to impinge on the wearer's neck. First and second strap attachment elements 250, 260 that are rotatable thus allow first and second strap attachment elements 250, 260 and straps 242a, 242b to generally conform to a particular wearer's head and neck and provide a comfortable fit on wearers having varying physical characteristics.

In an exemplary embodiment, an arcuate portion of second ring 263 of second strap attachment element 260 is able to slide within channel 252 and or groove 256 of first strap attachment element 250 such that first and second strap attachment elements 250, 260 are rotatable when attached. In an exemplary embodiment, first and second rings 253, 263 are circular rings defining circular openings 254, 264. In other exemplary embodiments, rings 253, 263 may be circular, elliptical, or otherwise exhibit a curved or arcuate portion defining first and second openings 254, 264 of any desired shape, such that first and second strap attachment elements 250, 260 may rotate relative to one another when attached. In an exemplary embodiment, first strap attachment element 250 can rotate at least 45° relative to second strap attachment element 260 while first and second attachment elements 250, 260 are attached. In various exemplary embodiments, in order to be positionable between a first configuration in which first strap attachment element 250 is attached only to the second attachment element, and a second configuration in which first strap attachment element 250 is attached to second strap attachment element 260 and lower attachment point 223 of strap support 220, first strap attachment element 250 must be able to rotate at least 30°, 60°, 90°, 120°, 150°, 180° or more than 180° relative to second strap attachment element 260.

Straps 242a, 242b and/or first and second strap attachment elements 250, 260 form an angle theta when in the first configuration of FIG. 3. First and second strap attachment elements 250, 260 are able to rotate to a natural position, as described above. In an exemplary embodiment, first and second strap attachment elements 250, 260 are thus positioned generally straight across the back of a wearer's neck. For example, theta may be between approximately 170° and 190°, between approximately 175° and 185°, or approximately 180°.

FIG. 4 shows first and second straps 242a, 242b in a second configuration in which first strap attachment element 250 is attached to second strap attachment element 260 and to attachment point 223 of strap support 220. Similar to the configuration of FIG. 3, first and second straps 242a, 242b are tensioned such that a respiratory protection device (not shown), for example, is maintained in a position of use over a nose and mouth of a wearer.

First and second central openings 254, 264, are positioned over attachment point 223. Central openings 254, 264 may exhibit a diameter similar or slightly smaller than an outer diameter D of flanged edge 224 such that first and second strap attachment elements 250, 260 may be pushed over outer portion 225 and be maintained on middle or inner portion 226 by the flanged edge 224. First and second strap attachments 250, 260 are rotatable relative to each other when attached to attachment point 223 of strap support 220. As described above, an arcuate portion of second ring 263 of second strap attachment element is able to slide within channel 252 and or groove 256 of first strap attachment element 250. The flanged projection passes through the first and second central openings 254, 264, and thus first and second strap attachment elements 250, 260 rotate about the middle or inert portion 226 when attached at attachment point 223.

Straps 242a, 242b and/or first and second strap attachment elements 250, 260 form an angle beta when in the second configuration of FIG. 4. First and second strap attachment elements 250, 260 are able to rotate to a natural position, as described above. In an exemplary embodiment, first and second strap attachment elements 250, 260 are thus generally angled downward as the first and second straps pass below each respective ear of a wearer towards a mask body of a respiratory protection device (not shown). Angles theta and beta may vary depending on the physical characteristics of a wearer, and/or the desired positioning and tensioning of first and second straps 242a, 242b. However, in an exemplary embodiment, angle beta formed by straps 242a, 242b and/or first and second strap attachment elements 250, 260 in the second position of FIG. 4 is less than an angle theta formed by straps 242a, 242b and/or first and second strap attachment elements 250, 260 in the first position of FIG. 3. In some exemplary embodiments, beta may be less than 170°, less than 160°, less than 120°, less than 90°, or less than 60°. In some exemplary embodiments, beta may be less than 45° less than theta, less than 60° less than theta, or less than 90° less than theta.

Figure 5:
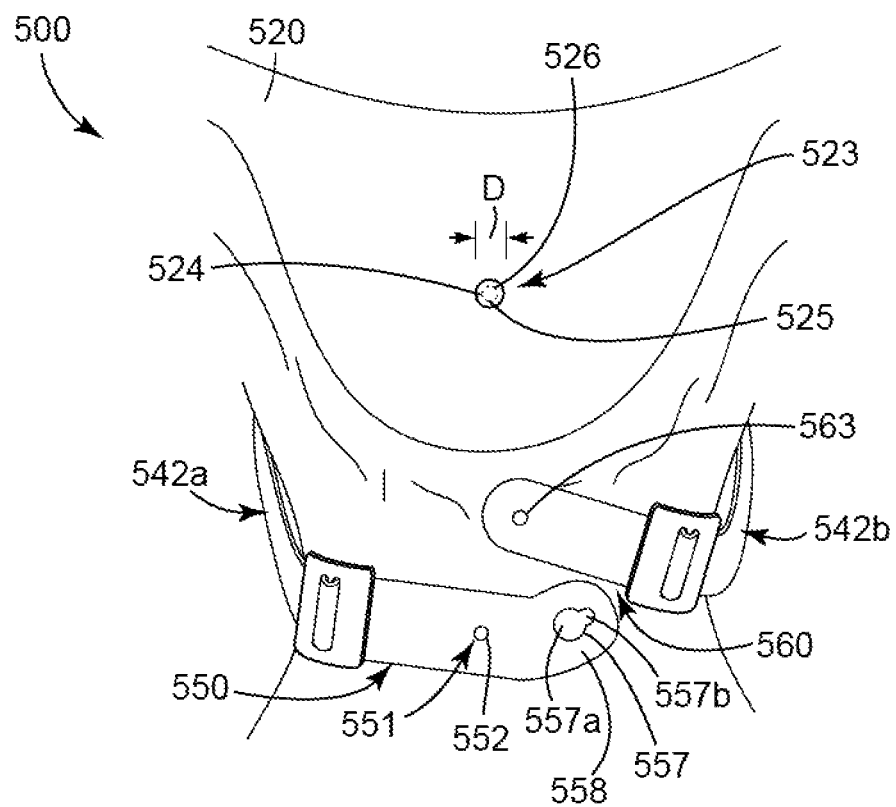
FIG. 5 shows a rear view of an exemplary harness assembly according to the present disclosure having exemplary first and second strap attachment elements in an unattached configuration.
Figure 6:
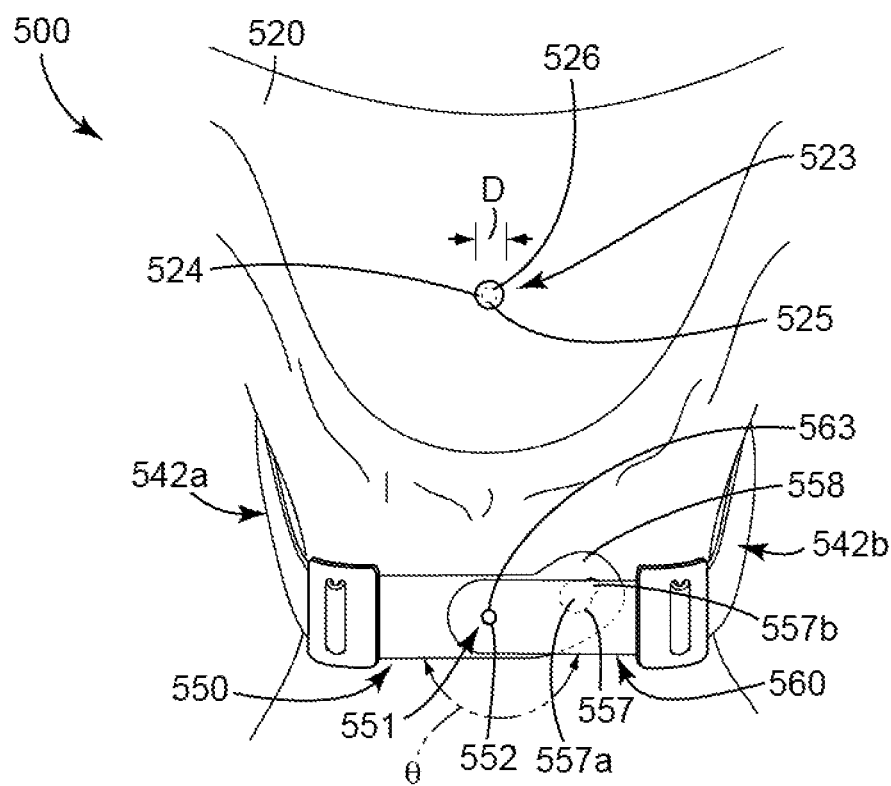
FIG. 6 shows a rear view of an exemplary harness assembly according to the present disclosure having exemplary first and second strap attachment elements in a first configuration in which the first and second strap attachment elements are attached.
Figure 7:
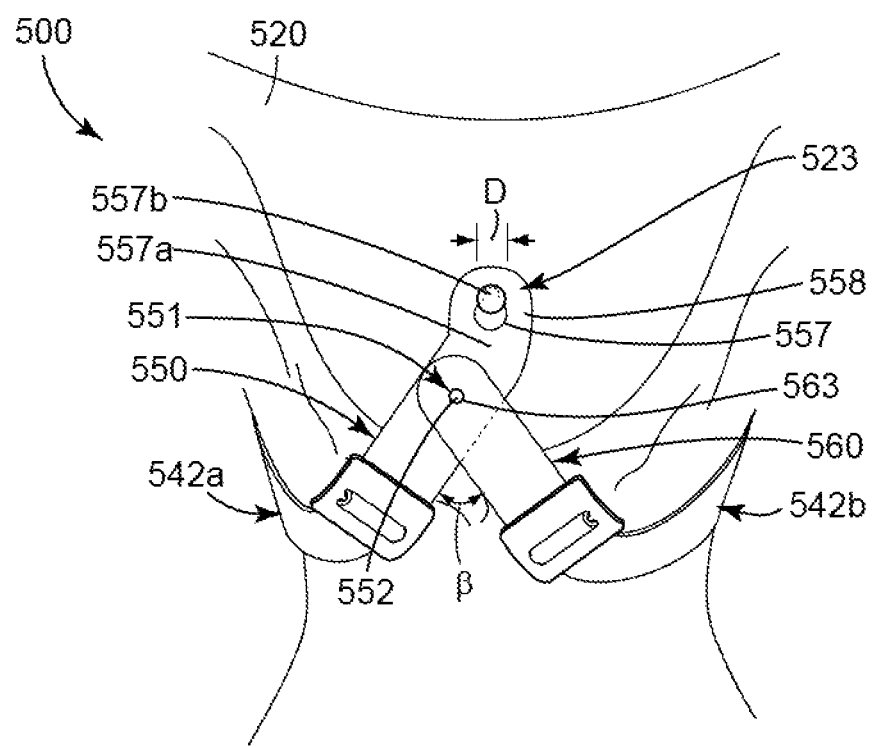
FIG. 7 shows a rear view of an exemplary harness assembly according to the present disclosure having exemplary first and second strap attachment elements in a second configuration in which the first attachment element is attached to the second attachment element and an attachment point of a strap support.

FIGS. 5, 6 and 7 show rear views of another exemplary embodiment of a harness assembly 500 including a strap support 520 having a lower attachment point 523, first lower strap 542a having a first strap attachment element 550, and second lower strap 542b having a second strap attachment element 560. FIG. 5 shows first and second straps 542a, 542b in an unattached configuration, just before being attached when a wearer is donning harness assembly 500, for example. FIG. 6 shows first and second straps 542a, 542b in a first configuration in which the first and second strap attachment elements 550, 560 are attached and a respiratory protection device, for example, may be maintained in a position of use over a nose and mouth of a wearer. FIG. 7 shows first and second straps 542a, 542b in a second configuration in which first strap attachment element 550 is attached to second attachment element 560 and to attachment point 523 of strap support 520 and a respiratory protection device, for example, may be maintained in a position of use over a nose and mouth of a wearer.

Similar to harness assembly 200 described above, first and second straps 542a, 542b include first and second strap attachment elements 550 and 560 proximate first and second end portions 543a, 543b. First strap attachment element 550 is attachable to second strap attachment element 560 and attachment point 523 of strap support 520. In an exemplary embodiment, first strap attachment element 550 includes first and second attachment features such that the first attachment feature is attachable to the second strap attachment element and the second attachment feature is attachable to attachment point 523. For example, first strap attachment element 550 may comprise a first attachment feature in the form of a projection 551 having a flange 552. In other exemplary embodiments, first attachment feature may be in the form of a loop, tab, hook, receptacle, or other suitable attachment feature. In an exemplary embodiment, second attachment feature is a keyed opening 557 defined by an angled end portion 558 of first strap attachment element 550. Keyed opening 557 includes a larger portion 557a and a smaller portion 557b.

Second strap attachment element 560 includes one or more attachment features having a shape complementary to an attachment feature of first strap attachment element 550. In an exemplary embodiment, second strap attachment element 560 includes an opening or recess 563. The opening or recess 563 is positionable on projection 551 of first strap attachment element 550. In an exemplary embodiment, projection 551 and/or a portion of second strap attachment element 560 defining opening or recess 563 is made of a resilient or flexible material such that opening or recess 563 may be pressed over flange 552 and maintained on projection 551.

Strap support 520 includes a lower attachment point 523 to which a strap attachment element may be attached. Lower attachment point 523 is positioned at a generally central location on strap support 520. For example, lower attachment point may be positioned proximate a sagittal plane (not shown), for example, that divides a wearer's head into imaginary left and right halves. A generally centrally located attachment point 523 allows both of first and second attachment elements to be attached to strap support 520 at a single location while first and second straps exhibiting a similar length. In the exemplary embodiment of FIGS. 5 through 7, lower attachment point 523 is a flanged projection extending outwardly from strap support 520. Lower attachment point 523 may have a generally cylindrical shape, for example, having a flanged edge 524 such that a diameter D at an outer portion 525 is greater than a diameter at a middle or inner portion 526. An opening or recess of a strap attachment element may be positioned over the flanged projection to attach one or more strap attachment elements to lower attachment point 523, as described in greater detail below. In other exemplary embodiments, a lower attachment point 523 may be provided in the form of a hook, loop, receptacle, shelf, or other suitable attachment point such that one or more strap attachment elements may be attached to strap support 520.

FIG. 6 shows first and second straps 542a, 542b in a first configuration in which first and second strap attachment elements 550, 560 are attached. First and second straps 542a, 542b are tensioned such that a respiratory protection device (not shown), for example, is maintained in a position of use over a nose and mouth of a wearer. Opening or recess 563 of second strap attachment element 560 is positioned on projection 551 of first strap attachment element 550. A flange 552 of projection 551 prevents disengagement between first and second strap attachment elements 550, 560. In an exemplary embodiment, tension of first and second lower straps 542a, 542b provides a force on the first and second strap attachment elements 550, 560 that may further prevent disengagement.

First and second strap attachments elements 550, 560 are rotatable when attached. That is, first strap attachment element 550 may rotate relative to second strap attachment element 560 when first and second strap attachment elements 550, 560 are attached. For example, opening or recess 563 is circular, elliptical, or otherwise defined by an arcuate portion such that the opening or recess 563 may rotate about projection 551 and vice versa. In an exemplary embodiment, first strap attachment can rotate at least 45° relative to second strap attachment element while first and second attachment elements are attached. In various exemplary embodiments, in order for first and second straps to be positionable between a first configuration in which first strap attachment element is attached only to the second attachment element, and a second configuration in which first strap attachment element 550 is attached to second strap attachment element 560 and lower attachment point 523 of strap support 520, first strap attachment element 550 must be able to rotate at least 30°, 60°, 90°, 120°, 150°, 180° or more than 180° relative to second strap attachment element 260.

Straps 542a, 542b and/or first and second strap attachment elements 550, 560 form an angle theta when in the first configuration of FIG. 6. First and second strap attachment elements 550, 560 are able to rotate to a natural position, as described above. In an exemplary embodiment, first and second strap attachment elements 550, 560 are thus positioned generally straight across the back of a wearer's neck. For example, theta may be between approximately 170° and 190°, between approximately 175° and 185°, or approximately 180°.

FIG. 7 shows first and second straps 542a, 542b in a second configuration in which first strap attachment element 550 is attached to second attachment element 560 and to attachment point 523 of strap support 520. Similar to the configuration of FIG. 6, first and second straps 542a, 542b are tensioned such that a respiratory protection device (not shown), for example, is maintained in a position of use over a nose and mouth of a wearer.

Keyed opening 557 defined by angled end 558 of first strap attachment element 550 is positioned over attachment point 523. Large opening 557a of keyed opening 557 may be similar in size to a large outer diameter D of flanged edge 524. The small opening 557b of keyed opening 557 may then slide downward over a middle or inner portion 526 of attachment point 523 such that first strap attachment element 550 is maintained on attachment point 523. First and second strap attachment elements 550, 560 are rotatable relative to each other when attached to attachment point 523 of strap support 520. As described above, opening or recess 563 of second strap attachment element 560 is able to rotate about a flanged projection 551, for example, of first strap attachment element 550.

Straps 542a, 542b and/or first and second strap attachment elements 550, 560 form an angle beta when in the second configuration of FIG. 7. First and second strap attachment elements 550, 560 are able to rotate to a natural position, as described above. In an exemplary embodiment, first and second strap attachment elements 550, 560 are thus generally angled downward as the first and second straps 542a, 542b pass below each respective ear of a wearer towards a mask body of a respiratory protection device (not shown). Angles theta and beta may vary depending on the physical characteristics of a wearer, and/or the desired positioning and tensioning of first and second straps 542a, 542b. However, in an exemplary embodiment, angle beta formed by straps 542a, 542b and/or first and second strap attachment elements 550, 560 in the second position of FIG. 7 is less that an angle theta formed by straps 542a, 542b and/or first and second strap attachment elements 550, 560 in the first position of FIG. 6. In some exemplary embodiments, beta may be less than 170°, less than 160°, less than 120°, less than 90°, less than 60°. In some exemplary embodiments, beta may be less than 45° less than theta, less than 60° less than theta, or less than 90° less than theta.

Figure 8:
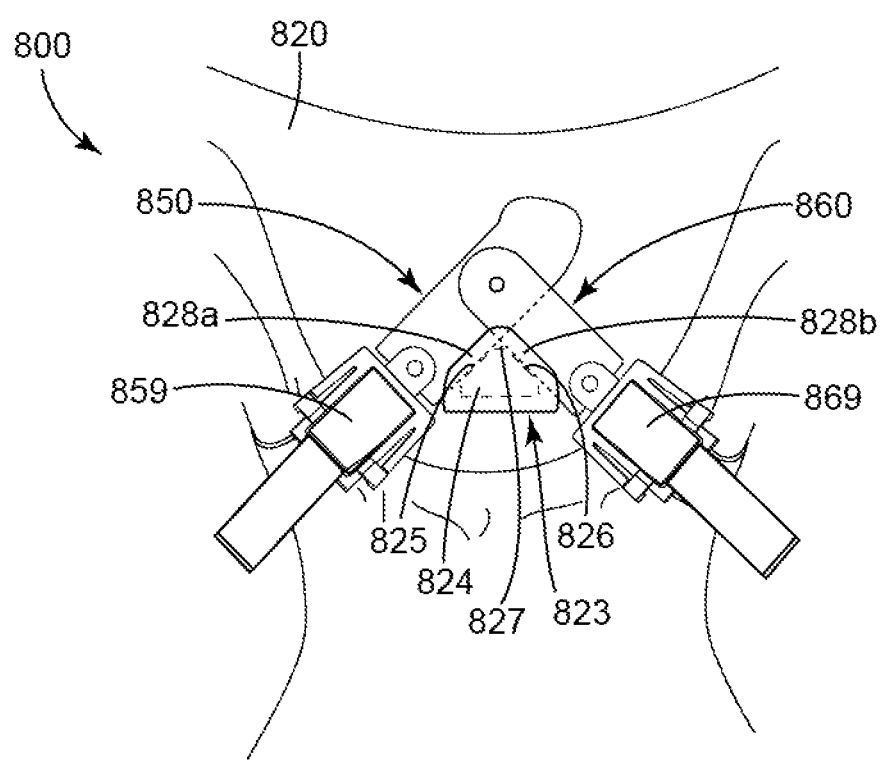
FIG. 8 shows a rear view of an exemplary harness assembly according to the present disclosure having exemplary first and second strap attachment elements in a second configuration in which the first attachment element is attached to the second attachment element and an attachment point of a strap support.

FIG. 8 shows another exemplary embodiment of a harness assembly 800 including a strap support 820 having a lower attachment point 823, first lower strap 842a having a first strap attachment element 850, and second lower strap 842b having a second strap attachment element 860. First and second straps 842a, 842b are in a second configuration in which first strap attachment element 850 is attached to second strap attachment element 860 and to attachment point 823 of strap support 820 and first and second straps 842a, 842b are tensioned such that a respiratory protection device (not shown), for example, is maintained in a position of use over a nose and mouth of a wearer.

Harness assembly 800 is similar to harness assembly 500, but lower attachment point 823 includes a stepped shelf 824 that first and second attachment elements 850, 860 may be attached to. Stepped shelf 824 includes first and second inner angled surfaces 825, 826, and an upwardly extending retaining surface 827 defining channels 828a, 828b. First and second strap attachment elements 850, 860 may be positioned between a surface of the stepped shelf 824 and strap support 820 such that first and second strap attachment elements 850, 860 rest on first and second inner angled surfaces 825, 826 in channels 828a, 828b. First and second straps 842a, 842b may exert a downward force that maintains the first and second strap attachment elements 850, 860 at attachment point 823.

In an exemplary embodiment, first and second strap attachment elements 850, 860 are rotatable relative to each other, and may rotate when positioned in the second configuration of FIG. 8 from a first configuration (not shown). In some exemplary embodiments, first and second attachment elements 850, 860 may comprise strap retaining devices 859, 859 to join straps 842a, 852b with first and second strap attachment elements 850, 860. Strap retaining devices 859, 869 may be integrally formed with strap attachment elements 850, 860, or subsequently joined. In an exemplary embodiment, strap retaining devices 859, 869 are rotatably connected to a portion of strap attachment elements 850, 860, such that strap retaining devices 859, 869 and straps 842a, 842b may pivot or rotate when strap attachment elements 850, 860 are attached at attachment point 823. In some exemplary embodiments, first and second strap attachment elements 850, 860 are permanently attached or attached such that rotation only occurs at strap retaining devices 859, 869. U.S. application Ser. No. 13/756,895, titled Personal Protective Equipment Strap Retaining Devices, and filed on the same date herewith, addresses various embodiments of exemplary strap retaining devices, and is incorporated herein by reference.

A harness assembly according to the present disclosure provides several advantages. A harness assembly including first and second strap retaining devices that are rotatable when attached, for example, allow a harness assembly to be positioned in multiple configurations. While prior harness assemblies were limited to providing straps in only one configuration, harness assemblies described herein allow a wearer to choose between a configuration in which lower straps pass about a wearer's neck, for example, or a configuration in which lower straps are attached to a strap support. A wearer may select a desired configuration to provide a suitable fit that is compatible with clothing, other personal protective devices, or the wearer's preference. Further, attachment elements including rings or arcuate portions defining one or more central openings allow quick, easy and secure attachment while allowing appropriate rotation such that straps may be positioned naturally about a wearer's neck and head. A harness assembly and attachment elements described herein may be suitable for half-face respirators, full-face respirators, powered or positive pressure respirators, and other suitable respiratory protection devices.

The foregoing detailed description and examples have been given for clarity of understanding only. No unnecessary limitations are to be understood there from. It will be apparent to those skilled in the art that many changes can be made in the embodiments described without departing from the scope of the disclosure. Any feature or characteristic described with respect to any of the above embodiments can be incorporated individually or in combination with any other feature or characteristic, and are presented in the above order and combinations for clarity only. Thus, the scope of the present disclosure should not be limited to the exact details and structures described herein, but rather by the structures described by the language of the claims, and the equivalents of those structures.

What is claimed is:

1. A harness assembly for a respiratory protection device, comprising:
    a strap support having an attachment point;
    a first strap having a first strap attachment element; and
    a second strap having a second strap attachment element;
    wherein the first strap attachment element is attachable to the second strap attachment element and attachable to the attachment point of the strap support, and the first and second straps are positionable between a first configuration in which the first strap attachment element is attached only to the second strap attachment element and a second configuration in which the first strap attachment element is attached to the second strap attachment element and the attachment point of the strap support.

2. The harness assembly of claim 1, wherein the first strap attachment element is rotatable relative to the second strap attachment element when the first and second strap attachment elements are attached.

3. The harness assembly of claim 1, wherein the first strap attachment element is rotatable relative to the second strap attachment element when the first strap attachment element is attached to the second strap attachment element and the attachment point of the strap support.

4. The harness assembly of claim 1, wherein the first and second strap attachment elements are permanently attached.

5. The harness assembly of claim 1, wherein the strap support is positionable about the crown of a wearer's head.

6. The harness assembly of claim 1, wherein the attachment point is positioned at a central location at the rear of the strap support.

7. The harness assembly of claim 1, wherein the strap support further comprises first and second upper attachment points positioned at side locations and a lower attachment point positioned at a central location at the rear of the strap support.

8. The harness assembly of claim 1, wherein the first strap attachment element comprises an attachment feature selected from the group consisting of a hook, a loop, a projection, a flange, and a recess.

9. The harness assembly of claim 1, wherein the first strap attachment element comprises first and second attachment features.

10. The harness assembly of claim 9, wherein the first attachment feature of the first strap attachment element is attachable to the second strap attachment element and the second attachment feature of the first strap attachment element is attachable to the attachment point of the strap support.

11. The harness assembly of claim 1, wherein the first strap attachment element comprises a first ring defining a first central opening.

12. The harness assembly of claim 11, wherein the second strap attachment element comprises a second ring defining a second central opening.

13. The harness assembly of claim 12, wherein the first and second central openings are substantially aligned when the first strap attachment element and the second strap attachment element are attached.

14. The harness assembly of claim 11, wherein the first strap attachment element comprises a hook proximate the ring and the hook maintains the first and second central openings in substantial alignment when the first strap attachment element and second strap attachment element are attached.

15. The harness assembly of claim 14, wherein the first ring comprises a groove and the second ring is positionable in the groove of the first ring.

16. The harness assembly of claim 11, wherein the first strap attachment element further comprises a flange extending about at least a portion of first central opening, and the flange maintains the first and second central openings in substantial alignment when the first strap attachment element and second strap attachment element are attached.

17. The harness assembly of claim 11, wherein the first strap attachment element may rotate relative to the second strap attachment element when the first and second strap attachment elements are attached.

18. The harness assembly of claim 1, wherein in the first configuration the first and second straps form an angle theta and in the second configuration the first and second straps form an angle beta.

19. The harness assembly of claim 18, wherein 170°<theta<190°.

20. The harness assembly of claim 18, wherein beta<theta.

21. The harness assembly of claim 18, wherein beta< [theta−45°].

22. The harness assembly of claim 18, wherein beta< [theta−90°].

23. A harness assembly for a respiratory protection device, comprising:
    a strap support positionable about a crown of a wearer's head and having first and second upper attachment points and a central lower attachment point;
    first and second upper straps attachable to the first and second upper attachment points;
    a first lower strap having a first strap attachment element; and
    a second lower strap having a second strap attachment element;
    wherein the first strap attachment element is attachable to the second strap attachment element and attachable to the lower attachment point of the strap support, and the first and second lower straps are positionable between a first configuration in which the first strap attachment element is attached only to the second strap attachment element and a second configuration in which the first strap attachment element is attached to the second strap attachment element and the lower attachment point.

24. A harness assembly for a respiratory protection device, comprising:
    a first lower strap having a first strap attachment element comprising a first ring defining a first central opening; and
    a second lower strap having a second strap attachment element comprising a second ring defining a second central opening;
    wherein the first strap attachment element is attachable to the second strap attachment element such that the first strap attachment element may rotate relative to the second strap attachment element when the first and second strap attachment elements are attached, and wherein the first and second central openings are substantially aligned when the first and second strap attachment elements are attached.

* * * * *